United States Patent [19]

Marx

[11] Patent Number: 4,790,300
[45] Date of Patent: Dec. 13, 1988

[54] DYNAMIC SPLINTING COMPONENT

[76] Inventor: Ralph H. Marx, 7714 N. 17th Pl., Phoenix, Ariz. 85020

[21] Appl. No.: 6,769

[22] Filed: Jan. 27, 1987

[51] Int. Cl.⁴ ............................................. A61F 5/04
[52] U.S. Cl. .................................... 128/84 C; 128/77; 128/87 C
[58] Field of Search ................. 128/84 C, 77, 87 C, 128/87 A, 88, 25 R, 26, 99, 103; 269/328

[56] References Cited

U.S. PATENT DOCUMENTS

| | | | |
|---|---|---|---|
| 3,707,463 | 1/1973 | Keropian | 128/26 |
| 3,769,970 | 11/1973 | Swanson | 128/87 A |
| 3,815,587 | 6/1974 | Guerrant | 128/77 |
| 4,370,976 | 2/1983 | Wanchik et al. | 128/77 |
| 4,409,970 | 10/1983 | Carrel | 128/84 |
| 4,602,620 | 7/1986 | Marx | 128/7.7 |
| 4,643,177 | 2/1987 | Sheppard et al. | 128/84 C |
| 4,660,550 | 4/1987 | Bodine | 128/77 |

FOREIGN PATENT DOCUMENTS

| | | | |
|---|---|---|---|
| 502687 | 5/1920 | France | 128/77 |
| 111276 | 11/1917 | United Kingdom | 128/77 |

OTHER PUBLICATIONS

Second Workshop Panel on Upper-Extremity Orthotics, Oct. 3, 1971, Hot Springs, Ark.

Primary Examiner—C. Fred Rosenbaum
Assistant Examiner—Mark F. Colosimo
Attorney, Agent, or Firm—Warren F. B. Lindsley

[57] ABSTRACT

A compact, low-profile, prefabricated dynamic splint component for use in treating certain wrist conditions or injuries. The component is mounted on the wrist and forearm by means of a wrist gauntlet. It subjects the hand to a perpendicular force that urges the hand upward about the wrist joint while avoiding the application of any compression forces to the wrist.

5 Claims, 2 Drawing Sheets

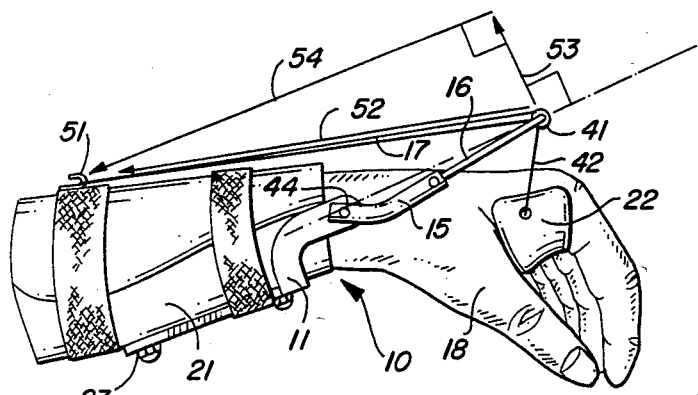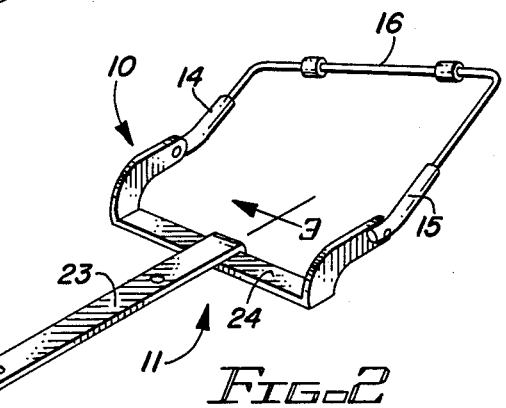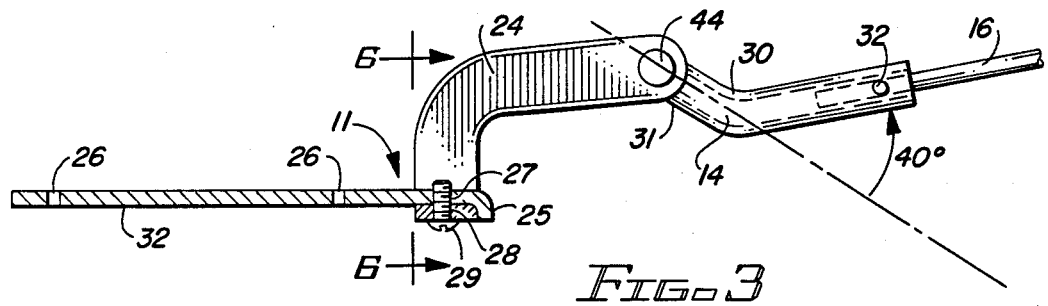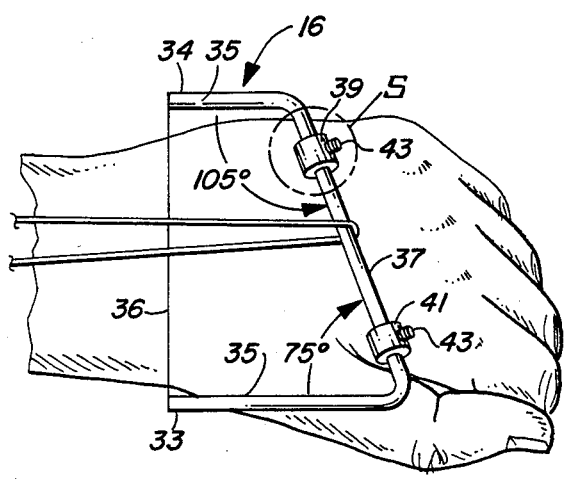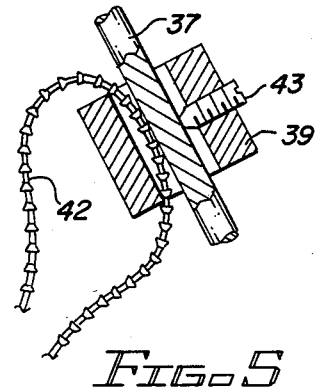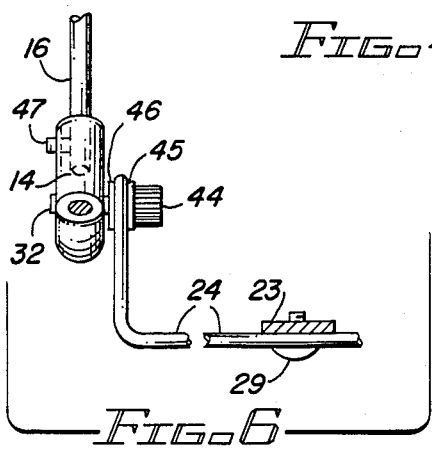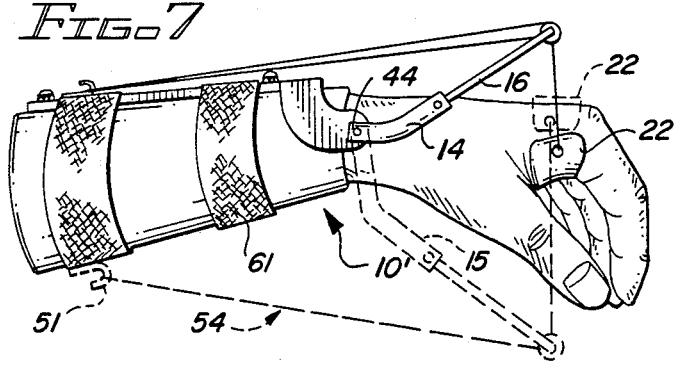

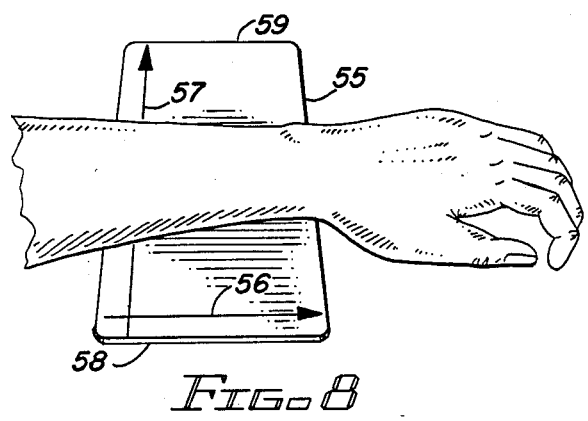
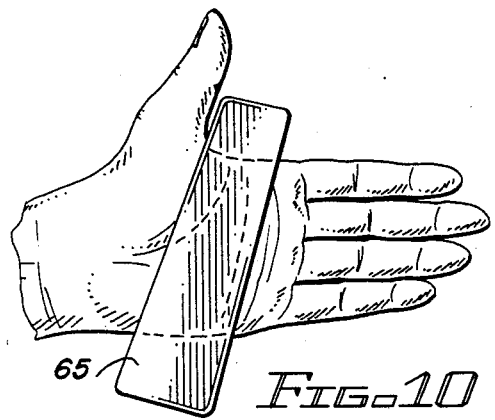
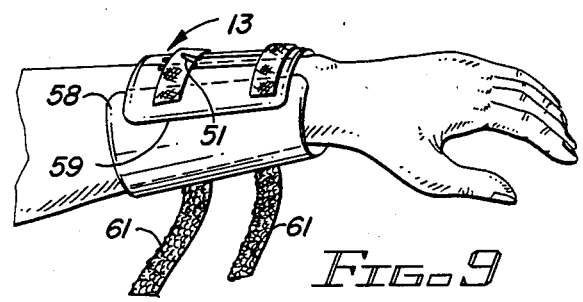
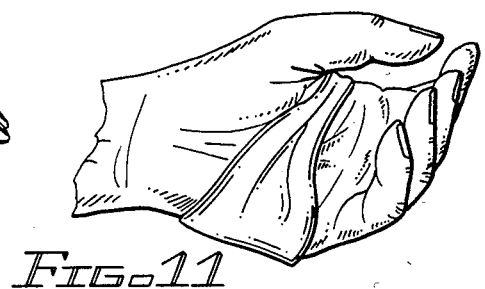
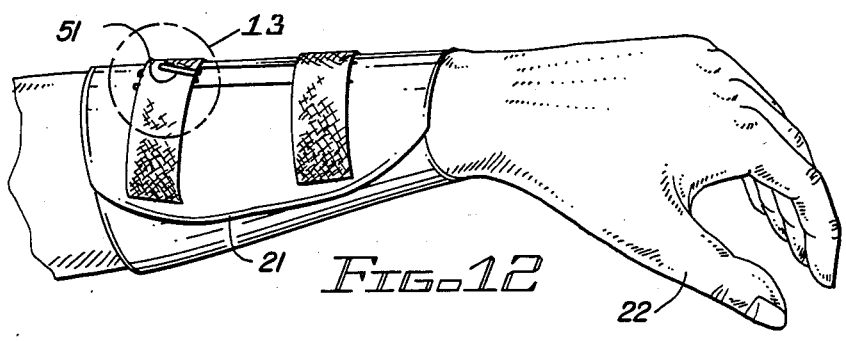
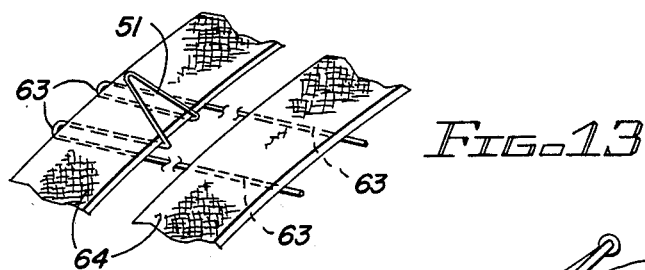
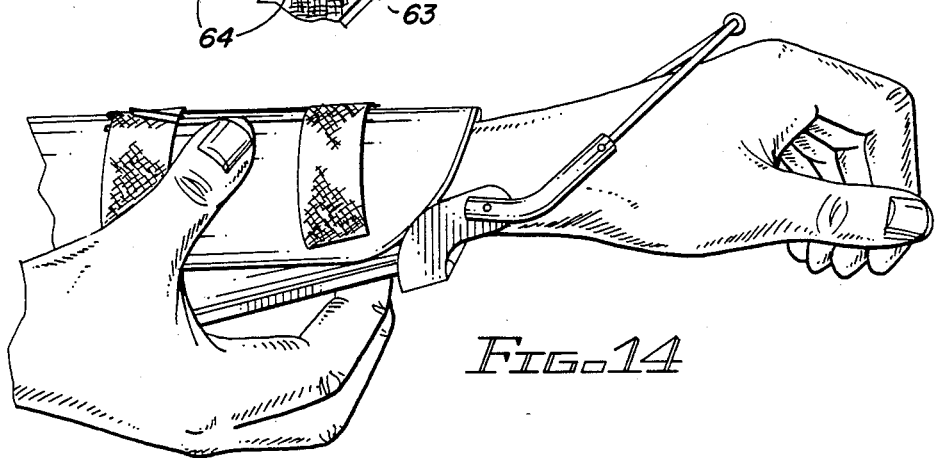

DYNAMIC SPLINTING COMPONENT

BACKGROUND OF THE INVENTION

To regain the full use of the wrist following various types of injuries, it is frequently found necessary or helpful to provide some form of physical therapy. This is especially true if the wrist has been confined for some time in a cast which tends to leave it in a stiff and weakened condition. Muscles associated with the bending or flexing of the wrist become atrophied, and the stiffened or enlarged tissues surrounding the joints interfere with the full motion of the joint system.

A particular form of therapy that is helpful in certain cases involves the controlled application of a force to the hand and wrist in a manner which draws the back of the hand upward toward a fully flexed position. Allowing the wrist to be flexed or bent in this manner tends to restore full freedom of movement while muscular resistance to the applied force restores tone and strength to the muscles.

Heretofore, there has not been available a suitable brace or appliance for such use. Makeshift braces and springs are typically too awkward and cumbersome to be worn under everyday living conditions.

What is needed is a compact, low-profile device that may be worn conveniently under typical conditions of work or recreation. In the provision of such a device, it is also important to insure that the device will not subject the wrist to compression or tension forces that are in some cases harmful to the joint and may only result in additional injury or an extended recovery period.

The present invention is directed toward the provision of a device of this type which may be applied to the wrist of a patient by a physician or physical therapist.

DESCRIPTION OF THE PRIOR ART

Various types of braces and appliances for therapeutic use in treating bone or muscle disorders are described in the prior art.

U.S. Pat. No. 4,409,970 discloses an apparatus and method for the treatment of communited Colles' fracture. The apparatus includes a kit comprising a wire bow, two stainless steel bone screws and an elastic band which are employed to place the fractured joint in traction to promote healing. The apparatus, when assembled, is incorporated into a cast which is formed over it.

U.S. Pat. No. 4,602,620 discloses a "Dynamic Outrigger Extension for Dorsal Wrist Splints" which employs adjustably positioned wheels mounted on a wire frame arranged immediately over the digits of a postoperative hand for precise alignment of dynamic splint forces following implant resection arthroplasty of the metacarpophalangeal joints. Such precise alignment of the digits and joints is essential to assure their proper alignment after healing.

The prior art devices do not address the need for a dynamic splint component with a capability for providing the desired rotational force to the wrist as an aid in restoring full strength and movement to an injured wrist.

SUMMARY OF THE INVENTION

In accordance with the invention claimed, a prefabricated dynamic splint component is provided for use in treating certain wrist conditions or injuries. The device is a compact, low profile structure that is intended to apply a rotational force to the wrist without subjecting the wrist joint to compression or tension.

It is, therefore, an object of the present invention to provide an improved dynamic splint component for use in treating certain types of wrist conditions or injuries.

Another object of this invention is to provide a dynamic splint component that is intended to be mounted upon the forearm and wrist of a patient for the purpose of applying a perpendicular force to the back of the hand, thereby to draw the hand upwardly as it flexes the wrist.

A further object of this invention is to provide a dynamic splint component which, in the process of applying such a flexing or torquing force to the wrist is constrained by virtue of its form and construction from applying compressive or tractive forces to the wrist structure.

A still further object of this invention is to provide a dynamic splint component in a form which may be readily applied to the forearm and wrist of a patient by a physician or physical therapist using commonly available splinting materials such as thermo plastics.

A still further object of this invention is to provide with such a dynamic splinting component a convenient and effective means for mounting the splinting component to the forearm and wrist of the patient.

Yet another object of this invention is to provide such a dynamic splinting component in a compact and low profile form so that it will not seriously interfere with the normal use of the hand and wrist of the patient.

Further objects and advantages of this invention will become apparent as the following description proceeds, and the features of novelty which characterize the invention will be pointed out with particularity in the claims annexed to and forming a part of this specification.

BRIEF DESCRIPTION OF THE DRAWINGS

The present invention may be more readily described with reference to the accompanying drawings, in which:

FIG. 1 is a perspective view showing the dynamic splint component of the invention secured to the wrist, forearm and hand of a patient;

FIG. 2 is a perspective view showing the prefabricated structure of the dynamic splint component;

FIG. 3 is a cross-sectional view of the structure of FIG. 2 as seen along line 3—3;

FIG. 4 is an enlarged view showing a member of the structure of FIG. 2 herein identified as the distal wire frame;

FIG. 5 is a cross-sectional view showing the construction of the portion of the distal wire frame enclosed in circular area 5 of FIG. 4;

FIG. 6 is a cross-sectional view of the structure of FIGS. 2 and 3 as seen along line 6—6 of FIG. 3;

FIG. 7 is a perspective view showing an alternate construction of the prefabricated structure of FIGS. 1-6;

FIGS. 8 and 9 illustrate sequential steps in the fabrication and preparation of the forearm and wrist gauntlet to which the prefabricated splint component is to be secured;

FIGS. 10 and 11 illustrate sequential steps in the preparation of the palmar sling by means of which the splint component applies a flexing force to the hand and wrist of the patient;

FIG. 12 shows the forearm and wrist gauntlet secured to the forearm and wrist of a patient;

FIG. 13 shows an enlarged view of the proximal hook as it is secured to the gauntlet, the hook being shown also in FIGS. 9 and 12 inside the areas enclosed by the circle 13 in both figures; and FIG. 14 illustrates the method by which the proper placement of the splint component upon the gauntlet is determined for the marking of mounting holes at the underside of the gauntlet.

DESCRIPTION OF THE PREFERRED EMBODIMENT

Referring more particularly to the drawings by characters of reference, FIGS. 1–6 disclose a dynamic splint component 10 embodying the invention and comprising a U-shaped or wishbone frame 11, left and right pivotal arms 14 and 15, distal wire frame 16 and tension band 17. Associated with component 10 and working in cooperation therewith upon the forearm, wrist and hand 18 of the patient are wrist gauntlet 21 and palmar sling 22.

In a first implementation of the invention, the wishbone frame 11 comprises a two-part metal structure in which a narrow metal strip 23 serves as the proximal leg of the wishbone and a specially formed U-shaped member 24 forms the two distal arms of the wishbone.

Strip 23 is approximately four and one-half inches long, one-half inch in width and one-eighth of an inch in thickness. The distal end of strip 23 is bent downward to form a one-eighth of an inch perpendicular projection 25 which is used for securing strip 23 to member 24. Holes 26 in strip 23 are provided, one near each of the proximal and distal ends of the strip for use in securing component 10 to a gauntlet 21. An additional hole 27 is provided adjacent projection 25 for use in securing strip 23 to member 24.

Member 24 is formed from a U-shaped stamping in which the legs of the "U" are approximately one and one-half inches long and are tilted slightly outwardly. The base of the "U" is approximately four inches in length. The width of the stamping is one-half inch and its thickness is one-eighth of an inch. The final form of member 24 is then obtained by placing the stamping on a horizontal surface and bending each of the two legs of the "U" upwardly through an angle of ninety degrees. The bends are made just inboard of the base of the legs at right angles to the base of the "U", as shown most clearly in FIG. 2.

As shown in FIGS. 2 and 3, member 24 is secured to the end of strip 23 by aligning hole 27 of strip 23 with a clearance hole 28 at the center of member 24. A screw 29 is then passed through hole 28 and threaded into hole 27. Projection 25 of strip 23 now wraps around the edge of member 24 preventing rotation of members 23 and 24, relative to each other.

The two pivotal arms 14 and 15 of the distal wire frame 16 are identical. Each is made from a two inch length of quarter inch outer-diameter hollow tubing. A bend 30 of approximately forty degrees is made at a point one-half inch from a first end 31 of the length of the tubing. One-quarter inch inboard from each end of the tubing, a hole 32 is drilled and tapped for a small screw such as an AWG #6 screw. The axes of the two holes are parallel with the axis of bend 30.

Distal wire frame 16 is made from a ten and one-half inch length of three-thirty-seconds of an inch diameter stiff wire. Both ends of the wire are bent towards each other in a common plane. One bend forms an inside angle of approximately 75 degrees at a point approximately three and one-quarter inches inboard from a first end 33; the other bend forms an inside angle of approximately 105 degrees at a point approximately two and one-quarter inches inboard from a second end 34 of the distal wire frame 16. The end segments 35 of the wire that are outboard from the two bends are parallel with each other and a line 36 joining the ends 33 and 34 is perpendicular with the two end segments 35. As shown in FIG. 4, the angles thus formed are intended to yield a configuration for the distal frame 16 such that when the end segments 35 are aligned with the longitudinal axis of the forearm and wrist, a center segment 37 of frame 16 will be aligned approximately with the palmar crease of hand 18 of the patient.

As shown in FIGS. 4 and 5, two tubular rings 39 and 41 are mounted on the center segment 37 of distal wire frame 16, the wire having been passed through the rings prior to the formation of the second bend. The inside diameter of the rings is sufficiently larger than the outside diameter of the wire to accommodate a nylon tie cord 42. Each of rings 39 and 41 may be locked into a desired position along segment 37 by means of a set screw 43 that turns into a threaded hole in the wall of the rings.

Assembly of the splint component 10 proceeds as follows: Strip 23 is first attached to member 24 as already described. The pivotal arms 14 and 15 are next pivotally secured to the ends of the two distal arms of member 24 as shown in FIGS. 2, 3 and 6 wherein a screw 44 is shown passing through a washer 45, a clearance hole in the end of the distal arm of member 24, a second washer 46 and is finally threaded into hole 32 at end 31 of each of pivotal arm 14 or 15. In the final step of the assembly operation, ends 33 and 34 of distal frame 16 are inserted into the free ends of the pivotal arms 14 and 15, and are secured therein by means of set screws 47 that are turned into holes 32 adjacent the free ends of arms 14 and 15.

The dynamic splint component 10 is intended to be supplied to physicians and physical therapists in the form as just described. The physician or therapist then mounts component 10 to the wrist, forearm and hand of the patient as shown in FIG. 1, using methods and materials yet to be described in the present disclosure.

As shown in FIG. 1, frame 11 is secured to the underside of wrist gauntlet 21 with strip 23 thereof directed rearwardly toward the patient's elbow and with the distal arms of member 24 curving upwardly and forwardly toward the dorsum of the hand. Arms 14 and 15 slope downwardly from their pivotal attachments at screws 44, then upwardly beyond bends 30. With proper positioning of the component 10, central segment 37 of frame 16 passes over the central portion of the dorsum of the hand 18, as shown in FIGS. 1 and 4, and the pivotal joint of component 10 is aligned with the center of rotation of the wrist for upward and downward movement of the hand. Component 10 is secured in this position to the wrist gauntlet 21 in a procedure to be described later. The hand sling 22 is then secured to frame 16 using two nylon ties 42, one at each side of the hand. Each of the ties passes through a hole at the edges of the hand sling 22 and through one of the rings 39 or 41 of frame 16. Rings 39 and 41 are then positioned to fit the hand and are secured by means of the set screws 43. Tension band 17 is then secured at one end to the center segment 37 of frame 16 and at the other end to a hook 51. Hook 51 is secured to the top side of the proximal end of gauntlet 21.

Band 17 is selected to provide the desired amount of force to frame 16. As shown in FIG. 1, frame 16 to which sling 22 is secured can only move rotationally with arms 14 and 15 about their pivotal mountings at screws 44. The only component of force that is applied to the hand is thus a perpendicular force directed upwardly from the dorsum of the hand, the perpendicular force urging rotation about screws 44.

FIG. 1 shows tension force 52 produced by band 17 as having a perpendicular component 53 and a longitudinal or compression component 54. The perpendicular component 53 is applied to the hand and wrist, while the splint component 10 supports the longitudinal component 54, so that no compression force is applied to the wrist of the user.

FIG. 7 shows a second embodiment of the invention in the form of a splint component 10'. Component 10' is nearly identical with component 10, except that it is designed to be secured to the dorsal or top side of the wrist and forearm rather than to the underside. This mounting arrangement, as shown in FIG. 7, is accommodated by turning frame 11 upside down relative to its position shown in FIG. 1, and reversing the angles of distal arms 14 and 15. With these changes, pivotal screw 44 is again aligned with the wrist joint and arms 14 and 15 together with frame 16 are again directed toward the desired position over the dorsum of the hand.

It should be recognized that either components 10 or 10' of FIGS. 1 and 7 may be mounted on the arm of a user below the wrist, as shown in dash lines in FIG. 7, to bias the hand in a downward direction and still fall within the scope of this invention.

The forming of wrist gauntlet 21 is illustrated in FIGS. 8 and 9. Gauntlet 21 may be made from any of the various splinting or casting materials such as a low temperature thermoplastic material. In the case of a thermoplastic material, a sheet of the material is first heated to a temperature at which it is pliable and easily cut and formed. The heated thermoplastic material 55 is then cut to the shape and dimensions relative to the wrist and forearm, as shown in FIG. 8, with a longitudinal (relative to the forearm) dimension 56 of approximately six inches and a lateral dimension 57 of approximately twelve inches. Gauntlet 21 is then formed by wrapping material 55 about the wrist and forearm with ends 58 and 59 overlapping on the top or dorsal side of the wrist and forearm. Appropriate ties 61, such as Velcro ® fasteners, are added to secure the gauntlet in position upon the wrist. The forming and construction of gauntlet 21 is completed by the addition of hook 51 which is secured to the top side of the gauntlet at its proximal end. As shown in FIGS. 9, 12 and 13, hook 51 may be formed from a length of wire with the center of the wire forming the hook, and the ends of the wire folded back upon themselves to form anchoring extensions 63 forward and aft of the hook. The hook may then be secured to the gauntlet material using a suitable adhesive tape 64.

Once gauntlet 21 has been formed and prepared for use as just described, it is allowed to cool to room temperature. At room temperature, it stiffens and retains its shape, but is still sufficiently flexible that its overlapping edges may be drawn apart and the gauntlet may then be removed from the wrist and then replaced again some time later.

Palmar sling 22 may be formed from the same type of thermoplastic material, as illustrated in FIGS. 10 and 11. As shown in FIG. 10, the heated thermoplastic material 65 is first cut into a strip approximately two inches wide and six inches long. In FIG. 11, material 65 has been formed to fit the contours of the palm of the hand, its ends extending at both sides of the hand and folded upwardly toward the dorsum. Holes are provided at both upwardly extending edges to receive nylon cords 42 which are to be held by rings 39 and 41 of distal frame 16. When sling 22 is formed in this manner to a particular patient's hand, it will retain its custom-fitted contours as it cools, and will fit the patient's hand comfortably throughout its use.

Gauntlet 21 and sling 22 having been formed as just described, are now positioned and secured upon the patient's forearm and wrist, as shown in FIG. 12. The assembled component 10 is then held in position, and its position adjusted for the desired alignment with the wrist and hand, as shown in FIG. 14. The desired locations of mounting holes 26 in strip 23 of frame 11 are then marked with a pencil on the under surface of gauntlet 21. Gauntlet 21 may then be removed from the patient's forearm so that holes may be punched or drilled at the marked locations. Component 10 is then secured to the underside of gauntlet 21 using screws at holes 26.

Gauntlet 21, with attached component 10, is then remounted upon the patient's wrist, as shown in FIG. 1. With the addition of tension band 17, which is connected between center segment 37 of frame 16 and hook 51, and with the addition of ties 42 which secure the ends of the palmar sling 22 to rings 39 and 41, the mounting of the dynamic splint component 10 is complete.

One feature of component 10, as mounted to the wrist and hand in the manner just described, is that as the hand is moved downward toward a rest position, tension force 52 and its longitudinal component 54 increase, but the perpendicular component 53 decreases toward zero. A rest position is thus afforded in which the hand and wrist are relieved of all external forces with component 10 fully supporting the tension force of band 17. As the hand and wrist are moved upwardly from the rest position and thence downwardly again toward the rest position, the perpendicular component 53 provides the desired restraint against downward rotation of the wrist that is helpful in the healing process.

An effective dynamic splint component is thus provided in accordance with the stated objects of the invention, and although but two embodiments of the invention have been illustrated and described, it will be apparent to those skilled in the art that various changes and modifications may be made therein without departing from the spirit of the invention or from the scope of the appended claims.

What is claimed is:

1. A low-profile dynamic splint device for mounting on the wrist and forearm of a user which subjects the associated hand to a perpendicular force about the wrist joint while substantially avoiding the application of any compression force to the wrist comprising:
   a first frame means having two spaced parallelly arranged pivotally mounted arms rigidly formed at their first ends to form a laterally extending proximal leg, a second frame means extending between the other ends of said arms, said arms each being bent in a common direction terminating in a plane, said second frame means comprising a wire, the end segments of which are bent in a common direction to lie in said plane connecting one to each of said arms and having a center section, a wrist mountable gauntlet, a first means for securing said leg to said gauntlet, a spring biasing means connected to said center section of said second frame means and a point on said gauntlet for rotating said arms in unison about a point on said first frame means toward said gauntlet, a palmar sling means for supporting the hand of a user, and a second means flexibly connecting said palmar sling means to said center section of said second frame means, whereby in use the component of force applied to the hand of a user by said spring means is substantially a perpendicular force directed outwardly from the dorsum of the associated hand of the user.

2. A low-profile dynamic splint device for mounting on the wrist and forearm of a user which subjects the associated hand to a perpendicular force about the wrist joint while substantially avoiding the application of any compression force to the wrist comprising:

a first frame means having two spaced parallelly arranged pivotally mounted arms of substantially the same length rigidly formed at their first ends to form a laterally extending proximal leg, a second frame means extending between the other ends of said arms, said arms each being bent in a common direction terminating in a plane, said second frame means comprising a wire, the end segments of which are of different lengths and bent in a common direction to lie in said plane connecting one with each of said arms and having a center section, a wrist mountable gauntlet, a first means for securing said leg to said gauntlet, a spring biasing means connected to said center section of said second frame means and a point on said gauntlet for rotating said arms in unison about a point on said first frame means toward said gauntlet, palmar sling means for supporting the palm of a user, and a second means flexibly connecting said palmar means to said second frame means, whereby in use the component of force applied to the hand of a user by said spring means is substantially a perpendicular force directed outwardly from the dorsum of the associated hand of the user.

3. The low-profile dynamic splint device set forth in claim 1 wherein:

said first frame means comprises a wishbone configuration.

4. The low-profile dynamic splint device set forth in claim 2 wherein:

said palmar sling means comprises a thermoplastic material contoured to the palm of the hand of a user, the ends of which fold upwardly toward the dorsum of the hand, and said second means comprises a flexible cord means for connecting each end of said palmar sling means to said center section of said second frame means.

5. The low-profile dynamic splint device set forth in claim 1 wherein:

said second frame comprises a U-shaped configuration, the legs of which are of different lengths with their free ends terminating in a common plane extending perpendicularly thereto.

* * * * *